United States Patent [19]

Baader et al.

[11] Patent Number: 5,240,921

[45] Date of Patent: Aug. 31, 1993

[54] CYCLIC PYRIDINE-2,4 AND -2,5-DICARBOXYLIC ACID DIAMIDES, PROCESSES FOR THEIR PREPARATION AND THEIR USE

[75] Inventors: Ekkehard Baader, Königstein an Taunus; Martin Bickel, Bad Homburg; Volkmar Günzler-Pukall, Marburg, all of Fed. Rep. of Germany

[73] Assignee: Hoechst Aktiengesellschaft, Frankfurt am Main, Fed. Rep. of Germany

[21] Appl. No.: 571,107

[22] Filed: Aug. 23, 1990

[30] Foreign Application Priority Data

Aug. 25, 1989 [DE] Fed. Rep. of Germany ....... 3928144

[51] Int. Cl.⁵ ................. C07D 243/04; C07D 267/08; C07D 401/14; A61K 31/44
[52] U.S. Cl. ..................... 514/211; 514/218; 514/227.8; 514/231.5; 514/232.2; 514/255; 514/340; 514/341; 514/342; 540/544; 540/575; 544/60; 544/78; 544/360; 546/275; 546/278; 546/280; 546/193; 546/194
[58] Field of Search ............... 546/193, 194, 275, 278, 546/280; 544/124, 360, 60, 53, 96, 78; 540/544, 575; 514/218, 211, 226.8, 227.8, 231.5, 232.2, 255, 340, 341, 342

[56] References Cited

U.S. PATENT DOCUMENTS 4,987,132 1/1991 Mase et al. .................... 514/252

5,037,839 8/1991 Bickel et al. .................... 514/354

FOREIGN PATENT DOCUMENTS 0278453 8/1988 European Pat. Off. ........... 514/354

OTHER PUBLICATIONS

S. Botros et al., Chemical Abstracts, vol. 108, 1988, p. 725, abstract No. 150265c.

E. Buhleier et al., Chem. Ber., vol. 112, 1979, pp. 559–566, Verlag Chemie, GmbH, Weinheim, Del.

*Primary Examiner*—Alan L. Rotman
*Attorney, Agent, or Firm*—Finnegan, Henderson, Farabow, Garrett & Dunner

[57] ABSTRACT

The invention relates to cyclic pyridine-2,4- and -2,5-dicarboxylic acid diamides of the formula I

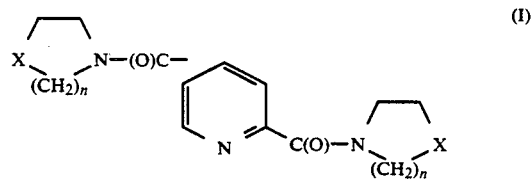

in which n and X have the meanings given. The compounds according to the invention inhibit proline hydroxylase and lysine hydroxylase and can accordingly be employed as fibrosuppressants and immunosuppressants.

9 Claims, No Drawings

CYCLIC PYRIDINE-2,4 AND -2,5-DICARBOXYLIC ACID DIAMIDES, PROCESSES FOR THEIR PREPARATION AND THEIR USE

Compounds which inhibit proline hydroxylase and lysine hydroxylase effect very selective inhibition of collagen biosynthesis by influencing collagen-specific hydroxylation reactions. In the course of these, protein-bonded proline or lysine is hydrolyzed by the enzymes proline hydroxylase and lysine hydroxylase. If this reaction is suppressed by inhibitors, a hypo-hydroxylated collagen molecule which is not capable of functioning and can be released by the cells into the extracellular space in only a small amount is formed. The hypo-hydroxylated collagen also cannot be incorporated into the collagen matrix and is very readily degraded proteolytically. As a consequence of these effects, the total amount of extracellularly deposited collagen is reduced.

It is known that inhibition of proline hydroxylase by known inhibitors, such as a,a'-dipyridyl, leads to an inhibition of the $Cl_q$-biosynthesis of macrophages (W. Müller et al., FEBS Lett. 90 (1978), 218; Immunbiology 155 (1978) 47). This results in a loss of the classical route of complement activation. Inhibitors of proline hydroxylase therefore also act as immunosuppressants, for example in immunity complex diseases.

It is known that proline hydroxylase is inhibited effectively by pyridine-2,4- and -2,5-dicarboxylic acid (K. Majamaa et al., Eur. J. Biochem. 138 (1984) 239–245). However, these compounds are effective as inhibitors in cell culture only in very high concentrations (Tschank, G. et al., Biochem. J. 238, 625–633, 1987). DE-A 3,432,094 describes pyridine-2,4- and -2,5-dicarboxylic acid diesters with 1–6 carbon atoms in the ester alkyl part as medicaments for inhibiting proline hydroxylase and lysine hydroxylase.

However, these lower alkyl diesters have the disadvantage that they are split too rapidly in the organism to give the acids and do not arrive at their site of action in the cell in a sufficiently high concentration, and therefore are not particularly suitable for possible administration as medicaments.

DE-A 3,703,959, DE-A 3,703,962 and DE-A 3,703,963 describe, in a general form, mixed esters/amides, higher alkylated diesters and diamides of pyridine-2,4- and 2,5-dicarboxylic acid which effectively inhibit collagen biosynthesis in the animal model.

The synthesis of N,N'-bis(2-methoxyethyl)-pyridine-2,4-dicarboxylic acid diamide and N,N'-bis(3-isopropoxypropyl)-pyridine-2,4-dicarboxylic acid diamide is thus described, inter alia, in DE-A 3,703,959.

An improved process for the preparation of N,N'-bis(2-methoxyethyl)-pyridine-2,4-dicarboxylic acid diamide is proposed in German Patent Applications P 38 26 471.4 and P 38 28 140.6. German Patent Application P 3924093.2 (HOE 89/F 241) proposes novel N,N'-bis-(alkoxy-alkyl)-pyridine-2,4-dicarboxylic acid diamides.

Surprisingly, it has now been found that cyclic pyridine-2,4- and -2,5-dicarboxylic acid diamides of the formula I

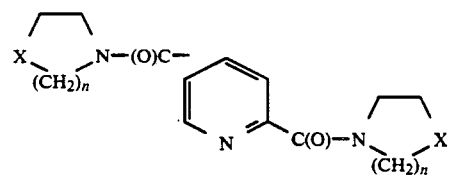

in which
n denotes 1 to 3 and
X denotes O, S or N—$R^1$
in which
$R^1$ denotes branched or unbranched $C_1$–$C_6$-alkyl, $C_1$–$C_6$-alkenyl or $C_1$–$C_6$-alkynyl, these alkyl, alkenyl and alkynyl radicals being unsubstituted or mono- or polysubstituted by:
phenyl, which is in turn mono- or polysubstituted by one or more substituents chosen from: halogen, nitro, cyano, carboxyl, hydroxyl, methyl, ethyl, methoxy, ethoxy and trifluoromethyl,
or
$N(R^2)_2$, in which
$R^2$ denotes H or $C_1$–$C_3$-alkyl,
or
$COOR^3$, in which
$R^3$ denotes H or $C_1$–$C_3$-alkyl,
or
$CON(R^4)_2$, in which
$R^4$ denotes H or $C_1$–$C_3$-alkyl, or in which $(R^4)_2$ represents a $C_4$–$C_6$-alkylene chain, in which no $CH_2$ group or a $CH_2$ group which is not directly adjacent to the nitrogen atom is replaced by O, S or N—R2,
or in which
$R^1$ denotes $C_1$–$C_4$-alkoxy-carbonyl or $C_3$–$C_7$-cycloalkyl and the physiologically tolerated salts,
likewise effectively inhibit lysine hydroxylase and proline hydroxylase in the animal model. It has also been found here, surprisingly, that in contrast to the compounds described in DE-A 3,703,959, DE-A 3,703,962 and DE-A 3,703,963, the compounds according to the invention exhibit a significantly better absorbability.

By halogen there are understood fluorine, chlorine, bromine and iodine.

"Polysubstituted" above and below means that at least 2 and at most all of the hydrogen atoms present in the alkyl, alkenyl, alkynyl and phenyl radicals are replaced by the substituents mentioned. In the case of polysubstitution, the substituents can also differ independently of one another.

The invention furthermore relates to a process for the preparation of compounds of the formula I, which comprises reacting
a compound of the formula II

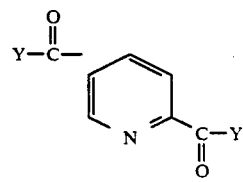

in which

Y is halogen or hydroxyl or together with the carbonyl group forms an active ester or a mixed anhydride, with a compound of the formula III

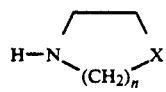

(III)

in which n and X have the meanings given above in the case of formula I, and, if appropriate, converting the reation products into their physiologically tolerated salts.

The preparation of compounds according to formula I and the preparation of the starting substances required for this—where these are not commercially available—are described in more detail below.

The compounds according to the invention are most easily prepared by mixing the two components, the pyridine derivative according to formula (II) and the amine according to formula (III), in equimolar amounts or with up to about a 5-fold excess of III, and reacting them at temperatures between $-30°$ and $150°$ C., preferably at $20°$ to $100°$ C., until the reaction has ended. The end of the reaction can be determined by means of thin layer chromatography (TLC control). One variant of this process comprises carrying out the reaction in a suitable solvent, such as diethyl ether, dimethoxyethane or tetrahydrofuran, chlorinated hydrocarbons, such as methylene chloride, chloroform or tri- or tetrachloroethylene, benzene, toluene or polar solvents, such as dimethylformamide or acetone or dimethyl sulfoxide. An excess of amine according to formula (III) of up to about 5 times the amount can also be used here. The reaction temperatures here are between room temperature and the boiling point of the solvent, temperatures in the range from room temperature to $130°$ C. being particularly preferred.

The reaction can likewise take place via a mixed anhydride, such as ethyl chloroformate, or via an activated ester, such as the paranitrophenyl ester (Y=ClCH$_2$—COO or NO$_2$—C$_6$H$_4$—O). Corresponding methods are described in the literature.

If appropriate, the reaction can also be carried out in the presence of bases. Possible additional bases are inorganic acid-trapping agents, such as carbonates or bicarbonates, for example sodium carbonate, potassium carbonate, sodium bicarbonate or potassium bicarbonate, or organic acid-trapping agents, such as tertiary amines, such as triethylamine, tributylamine or ethyl diisopropylamine, or heterocyclic amines, such as N-alkyl-morpholine, pyridine, quinoline or dialkylanilines.

The reaction of the compounds according to formula (II) with amines according to formula (III) is preferably carried out with the addition of a dehydrating agent, such as dialkylcarbodiimide, the alkyl radicals containing 1 to 8 carbon atoms and it also being possible, in the case of the C$_3$-C$_8$-compounds, for the alkyl radicals to be branched or cyclic; dicyclohexylcarbodiimide is preferably used. A corresponding method is described in the literature.

If appropriate, the products can be worked up, for example, by extraction or by chromatography, for example over silica gel. The isolated product can be recrystallized and if appropriate reacted with a suitable acid to give a physiologically tolerated salt. Examples of possible suitable acids are: mineral acids, such as hydrochloric and hydrobromic acid, as well as sulfuric, phosphoric, nitric or perchloric acid, or organic acids, such as formic, acetic, propionic, succinic, glycolic, lactic, malic, tartaric, citric, maleic, fumaric, phenylacetic, benzoic, methanesulfonic, toluenesulfonic, oxalic, 4-aminobenzoic, naphthalene-1,5-disulfonic or ascorbic acid.

The starting compounds of the formula (III), where they are not commercially available, can be synthesized in a simple manner (for example Organikum, Organisch Chemisches Grundpraktikum (Basic Practical Organic Chemistry), 15th edition, VEB Deutscher Verlag der Wissenschaften, 1976; a review of the various possibilities is to be found in the Method Register, page 822).

The starting compounds of the formula (II) are obtained, for example, by converting pyridine-2,4- or -2,5-dicarboxylic acid into the corresponding pyridine-2,4- or -2,5-dicarboxylic acid halide, preferably chloride (by processes which are known from the literature), which is then reacted with a suitable alcohol, for example paranitrobenzyl alcohol, to give the corresponding active ester. The pyridine-2,4- or -2,5-dicarboxylic acid can likewise also first be converted into a mixed anhydride, with the addition of a suitable carboxylic acid or a carboxylic acid ester, such as ethyl chloroformate, and the product is then reacted with the amines (III) to give the products according to the invention. A corresponding method is described in the literature.

The compounds of the formula I according to the invention have valuable pharmacological properties and in particular exhibit an activity as inhibitors of proline hydroxylase and lysine hydroxylase, and as a fibrosuppressant and immunosuppressant.

The activity of the fibrogenase can be determined by radioimmunological assay of the N-terminal propeptide of collagen type III or the N- or C-terminal crosslinking domains of collagen type IV (7s-collagen or type IV collagen-NC$_1$) in the serum.

For this purpose, the hydroxyproline, procollagen-III-peptide, 7s-collagen and type IV collagen-NC$_1$ concentrations in the liver of a) untreated rats (control)

b) rats to which carbon tetrachloride had been administered (CCl$_4$ control)

c) rats to which first CCl$_4$ and then a compound according to the invention had been administered, were measured (this test method is described by Rouiller, C., Experimental toxic injury of the liver; in The Liver, C. Rouiller, Volume 2, pages 335–476, New York, Academic Press, 1964).

The compounds of the formula I can be used as medicaments in the form of pharmaceutical preparations which contain them, if appropriate together with tolerated pharmaceutical excipients. The compounds can be used as medicines, for example in the form of pharmaceutical preparations containing these compounds as a mixture with a pharmaceutical organic or inorganic excipient suitable for enteral, percutaneous or parenteral administration, such as, for example, water, gum arabic, gelatin, lactose, starch, magnesium stearate, talc, vegetable oils, polyalkylene glycols, white petroleum jelly and the like.

The pharmaceutical preparations can be in the solid form, for example as tablets, coated tablets, suppositories or capsules; in the semi-solid form, for example as ointments, or in the liquid form, for example as solutions, suspensions or emulsions. If appropriate, they are sterilized and/or contain auxiliaries, such as preservatives, stabilizers, wetting agents or emulsifying agents, salts for modifying the osmotic pressure or buffers. They can furthermore also contain other therapeutically active substances.

The invention is illustrated in more detail with the aid of examples below:

EXAMPLE 1

2,4-Di-[(thiomorpholin-1-yl)-carbonyl]-pyridine 5 g (0.03 mol) of pyridine-2,4-dicarboxylic acid are suspended in 100 ml of toluene. 4.4 ml (0.06 mol) of thionyl chloride +1 ml of dimethylformamide are added dropwise at room temperature. The mixture is boiled under reflux for 2 hours until the resulting evolution of gas has ended and the solution has become clear. It is cooled to 0° C. and a solution of 60 ml (0.06 mol) of thiomorpholine and 10.4 ml (0.075 mol) of triethylamine in 20 ml of toluene is added dropwise.

The mixture is stirred at room temperature for 12 hours and washed once with saturated sodium bicarbonate solution. The aqueous phase is extracted twice more by shaking with toluene and the combined organic phases are dried over magnesium sulfate and evaporated. The residue is triturated with diethylether and filtered off with suction.

Yield: 5.2 g Melting point: 117°–119° C.

$^1$H-NMR: $\delta = 2.47$–2.93 (m, 8 H); 3.53–4.15 (m, 8 H); 7.25 (m, 1 H); 7.60 (m, 1 H); 8.70 (m, 1 H);

EXAMPLE 2

2,4-Di-[(morpholin-1-yl)-carbonyl]-pyridine

The acid chloride is prepared and reacted with 5.3 ml (0.06 mol) of morpholine analogously to Example 1.

Yield: 6.7 g Melting point: 126°–127° C.

$^1$H-NMR: $\delta = 3.50$–4.00 (m, 16 H); 7.30 (m, 1 H); 7.70 (m, 1 H); 8.70 (m, 1 H)

EXAMPLE 3

2,4-Di-[(1-methylpiperazin-4-yl)-carbonyl]-pyridine

The acid chloride is prepared and reacted with 6.7 ml (0.06 mol) of N-methylpiperazine analogously to Example 1.

Yield: 6.7 g Melting point: 125° C.

$^1$H-NMR: $\delta = 2.30$ (s, 6 H); 2.40 (m, 4 H); 2.5 (m, 4 H); 3.40 (m, 2 H); 3.60 (m, 2 H); 3.80 (m, 4 H); 7.30 (m, 1 H); 7.60 (m, 1 H); 8.65 (m, 1 H)

We claim:

1. A cyclic pyridine-2,4- or -2,5-dicarboxylic acid diamide of the formula I

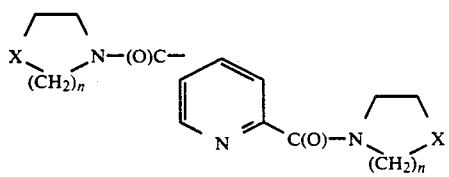

(I)

in which
n denotes 1 to 3 and
X denotes O, S or N—$R^1$
in which
$R^1$ denotes branched or unbranched $C_1$–$C_6$-alkyl, unsubstituted or monosubstituted by phenyl, which is in turn mono- or disubstituted by one or more substituents selected from halogen, nitro, hydroxyl, methyl, ethyl, methoxy, ethoxy and trifluoromethyl,
or
$R^1$ denotes $N(R^2)_2$, in which
$R^2$ denotes H or $C_1$–$C_3$-alkyl,
or
$R^1$ denotes $COOR^3$, in which
$R^3$ denotes H or $C_1$–$C_3$-alkyl,
or
$R^1$ denotes $CON(R^4)_2$, in which
$R^4$ denotes H or $C_1$–$C_3$-alkyl, or in which $(R^4)_2$ represents a $C_4$–$C_6$-alkylene chain, in which no $CH_2$ group or a $CH_2$ group which is not directly adjacent to the nitrogen atom is replaced by O, S or N—$R^2$, or in which
$R^1$ denotes $C_1$–$C_4$-alkoxy-carbonyl or $C_3$–$C_7$-cycloalkyl,
or a physiologically tolerated salt thereof.

2. A cyclic pyridine-2,4- or -2,5-dicarboxylic acid diamide of the formula I as claimed in claim 1, in which at least one of the following conditions is met:
$R^1$ denotes
branched or unbranched $C_1$–$C_6$-alkyl, unsubstituted or monosubstituted by phenyl,
which in turn is mono- or disubstituted by one or more substituents selected from fluorine, chlorine, methyl, ethyl, methoxy, ethoxy and trifluoromethyl,
$R^2$ denotes H or $C_1$–$C_2$-alkyl,
$R^3$ denotes H or $C_1$–$C_2$-alkyl,
$R^4$ denotes H or $C_1$–$C_2$-alkyl or
$(R^4)_2$ denotes a $C_4$–$C_5$-alkylene chain, in which no $CH_2$ group or a $CH_2$ group which is not directly adjacent to the nitrogen atom is replaced by O, S or N—$R^2$.

3. A cyclic pyrridine-2,4- (sic) or -2,5-dicarboxylic acid diamide of the formula I as claimed in claim 1, in which at least one of the following conditions is met:
$R^1$ denotes branched or unbranched $C_1$–$C_6$-alkyl, $C_1$–$C_4$-alkoxy-carbonyl or $C_3$–$C_7$cycloalkyl.

4. A cyclic pyridine-2,4- or -2,5-dicarboxylic acid diamide of the formula I as claimed in claim 1, in which at least one of the following conditions is met:
n denotes 2
X denotes O or S.

5. A pharmaceutical composition comprising an effective amount of a compound of the formula I as claimed in claim 1 or a physiologically tolerated salt thereof together with a suitable carrier, adjuvant or excipient.

6. A method for inhibiting proline hydroxylase and lysine hydroxylase which comprises administering to a host a pharmaceutical composition as claimed in claim 5.

7. A method for treating a host in need of a fibrosuppressant and immunosuppressant which comprises administering to said host a pharmaceutical composition as claimed in claim 5.

8. A method for inhibiting proline hydroxylase and lysine hydroxylase which comprises administering to a host an effective amount of a compound of the formula I as claimed in claim 1 or a physiologically tolerated salt thereof.

9. A method for inhibiting proline hydroxylase and lysine hydroxylase which comprises administering to a host an effective amount of a compound of the formula I as claimed in claim 1 or a physiologically tolerated salt thereof.

* * * * *